(12) United States Patent
Widenmeyer et al.

(10) Patent No.: US 9,366,658 B2
(45) Date of Patent: Jun. 14, 2016

(54) APPARATUS AND METHOD FOR IDENTIFYING A $CO_2$ CONTENT OF A FLUID

(71) Applicant: Robert Bosch GmbH, Suttgart (DE)

(72) Inventors: Markus Widenmeyer, Schoenaich (DE); Martin Schreivogel, Bad Berka (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 14/693,215

(22) Filed: Apr. 22, 2015

(65) Prior Publication Data
US 2015/0308997 A1 Oct. 29, 2015

(30) Foreign Application Priority Data
Apr. 25, 2014 (DE) .......... 10 2014 207 862

(51) Int. Cl.
*G01N 33/00* (2006.01)
*G01N 27/12* (2006.01)
(Continued)

(52) U.S. Cl.
CPC ......... *G01N 33/004* (2013.01); *B01J 20/28097* (2013.01); *B01J 20/3204* (2013.01); *B01J 20/3248* (2013.01); *B01J 20/3285* (2013.01); *C04B 38/009* (2013.01);
(Continued)

(58) Field of Classification Search
CPC ........... Y10T 436/145555; Y10T 436/147777; Y10T 436/17; Y10T 436/173845; Y10T 436/174614; Y10T 436/20; Y10T 436/203332; Y10T 436/204165; Y10T 436/204998; Y10T 436/25; Y10T 436/25875; G01N 1/22; G01N 1/2214; G01N 1/2273; G01N 27/02; G01N 27/04; G01N 27/12; G01N 27/125; G01N 27/22; G01N 27/227; G01N 33/0004; G01N 33/0009; G01N 33/004
USPC ............. 436/96, 98, 106, 111, 112, 127, 131, 436/132, 133, 147, 149, 150, 151, 181; 422/82.01, 82.02, 83, 88, 90, 98
See application file for complete search history.

(56) References Cited

U.S. PATENT DOCUMENTS 3,431,771 A * 3/1969 Tsien ..................... G01N 27/06 73/25.03
4,474,648 A * 10/1984 Tantram ............. G01N 27/4045 204/415

(Continued)

FOREIGN PATENT DOCUMENTS

DE 102 08 648 9/2003
DE 10 2010 014008 10/2011

*Primary Examiner* — Maureen Wallenhorst
(74) *Attorney, Agent, or Firm* — Norton Rose Fulbright US LLP

(57) ABSTRACT

An apparatus and a method for identifying a $CO_2$ content of a fluid. The apparatus includes: an absorber device having a porous material, the absorber device being capable of being brought into contact with the fluid; pores of the porous material having at least one hydrophilic first chemically functional group; the first chemically functional group being joined to the porous material; the first chemically functional group having the property of reacting in alkaline fashion with water; an electrode device that is disposed on the absorber device for electrical contacting of the absorber device; and an evaluation device that is electrically connected to the electrode device and by which an electrical property of the absorber device is measurable to identify the $CO_2$ content of the fluid.

17 Claims, 3 Drawing Sheets

(51) Int. Cl.
  *C04B 38/00* (2006.01)
  *B01J 20/28* (2006.01)
  *B01J 20/32* (2006.01)
  *G01N 1/22* (2006.01)
  *C04B 111/00* (2006.01)

(52) U.S. Cl.
  CPC ... *G01N 27/125* (2013.01); *C04B 2111/00991* (2013.01); *G01N 1/2214* (2013.01); *Y10T 436/204998* (2015.01); *Y10T 436/25875* (2015.01)

(56) References Cited

U.S. PATENT DOCUMENTS

| | | |
|---|---|---|
| 8,590,366 B2 | 11/2013 | Park et al. |
| 2012/0028846 A1 | 2/2012 | Yaghi et al. |
| 2013/0145935 A1* | 6/2013 | Suzuka .............. C08G 73/0266 96/234 |
| 2015/0073164 A1* | 3/2015 | Nomura ................. C07C 47/02 556/115 |

* cited by examiner

APPARATUS AND METHOD FOR IDENTIFYING A $CO_2$ CONTENT OF A FLUID

RELATED APPLICATION INFORMATION

The present application claims priority to and the benefit of German patent application no. 10 2014 207 862.8, which was filed in Germany on Apr. 25, 2014, the disclosure of which is incorporated herein by reference.

FIELD OF THE INVENTION

The present invention relates to an apparatus and a method for identifying a $CO_2$ content, i.e. a carbon dioxide content, of a fluid. The fluid can be a liquid or a gas, for example air. The invention relates in particular to an apparatus and a method for identifying a $CO_2$ content in the air in a living space or in a vehicle passenger compartment.

BACKGROUND INFORMATION

Identification of a carbon dioxide content of a fluid, for example in the air in a living space or in a vehicle passenger compartment, is a frequent task. On the basis of such measurements, for example, ventilation systems can be controlled in energy-efficient fashion.

Patent document U.S. Pat. No. 8,590,366 B2 discusses an apparatus for measuring a carbon dioxide concentration for a vehicle. An interior panel of the vehicle in which a carbon dioxide sensor apparatus is installed has an air entry conduit. The carbon dioxide sensor apparatus contains a light-emitting unit and a light-receiving unit, which are surrounded by a housing. The light emitted from the light-emitting unit passes through air that enters through the light entry conduit, and then strikes the light-receiving unit. The carbon dioxide concentration can be identified by evaluating the received light.

Patent document US 2012/0 028 846 A1 discusses a gas sensor that has a sensor region made of a porous framework for binding a gaseous analyte. A converter converts a change in the sensor region into a detectable property with which an absorbed or adsorbed gaseous analyte is measured.

Patent document DE 102 08 648 A1 discusses a sensor for identifying gases and a method for manufacturing said sensor. The sensor has a measurement electrode and a reference electrode, as well as a polymer layer that is in contact with the gas mixture and with the measurement electrode. A pH-sensitive electrode is provided as a measurement electrode.

Patent document DE 10 2010 014 008 A1 discusses an apparatus for isolating analytes from a expiration volume. The apparatus encompasses a carrier structure for capturing and collecting a breath condensate from the expiration volume.

SUMMARY OF THE INVENTION

The present invention discloses an apparatus having the features described herein and a method having the features described herein.

Evaluation can encompass, in particular, comparison of the measured electrical property with predetermined comparison values. For this, corresponding predetermined comparison values and/or properties of the fluid can be stored in a data memory connected to the evaluation device.

The electrical property can be, for example, an electrical conductivity, an impedance, or a capacitance. Evaluation can be accomplished in single-point fashion, regularly, or continuously. In particular, a change over time in the electrical property, for example a change in conductivity or a change in capacitance, can be measured and evaluated. Known chemical and/or physical properties of the fluid can be taken into consideration if the fluid whose $CO_2$ content is to be measured is already known, for example in the context of programming of the evaluation device.

The present invention implements a technically simple and economically implementable approach to measuring carbon dioxide concentrations.

What is used in the absorber device is a porous material that is equipped in its pores with at least one chemically functional group, for example an amino group, that reacts in, for example moderately strongly, alkaline fashion. The term "at least one group" is to be understood, when used here and hereinafter, to mean in particular that a plurality of such chemically functional groups can also be provided. The plurality of chemically functional groups can be made up of entirely identical chemically functional groups, but also of ones of different kinds. In other words, at least one kind of chemically functional group is present in or on the pores of the porous material, the chemically functional group reacting in alkaline fashion with water.

The at least one chemically functional group is immobilized, i.e. bound immovably, for example covalently, on a surface of the absorber device. A "surface" is to be understood here and hereinafter in particular as a surface constituted by the pores of the porous material.

The absorber device can be made up completely of a one-part absorber made of the porous material.

The pores of the absorber device can be, in particular, mesopores and can have, for example, a pore diameter between 2 nm and 50 nm. Mesopores have the advantage that they promote the phenomenon of capillary condensation.

Periodically mesoporous silica materials, e.g. MCM-41 or MCM-48, can be selected, for example, for the porous material. These have pore diameters of a few nanometers. Gas species condense in such materials, for example, at 0.2 times the partial pressure of the dew point.

Particularly advantageously, the porous material is selected so that as a result of capillary condensation, liquid water collects in the pores and remains there. A quantity of hydrogen carbonate ions is present in the liquid water as a function of a $CO_2$ partial pressure of the fluid, e.g. of air, and inter alia as a function of an alkaline strength, an alkaline density, and a temperature of the fluid. The moderate alkaline strength of the at least one immobilized chemically functional group can lead to the presence of a buffer system at a baseline $CO_2$ level of at least approx. 400 ppm. The buffer system can be, for example, an amine/ammonium-hydrogen carbonate buffer system. A concentration of $OH^-$ ions can thereby be approximately a few orders of magnitude lower than a concentration of the hydrogen carbonate ions. The hydrogen carbonate ions thus contribute predominantly to the conductivity of the absorber device, in particular of the porous material. A $CO_2$ content of the fluid can thus be identifiable, for example, by conductometry, i.e. by measuring conductivity.

Advantageously, more than 50% of the pore volume of the porous material is constituted by pores having diameters in the range from 1 nm to 500 nm.

The selection of suitable materials for the absorber device is to be adapted in general to the respective fluid and to the respective environmental parameters. Such environmental parameters can encompass, for example, a average expected $CO_2$ content, an average expected fluid temperature of the fluid, an average expected pressure of the fluid, etc. Selection of the suitable materials can also be adapted to expected minimum and/or maximum values, rather than the aforementioned average values, for the environmental parameters.

The electrode device can have electrodes that can be made, for example, of platinum, gold, silver, or aluminum. The electrodes can be applied onto two opposite sides, i.e. onto sides facing away from one another, of a continuous material quantity of the porous material.

The porous material can furthermore be applied onto a double-comb-like interdigital structure. The porous material can be present in compact fashion or as a layer.

The evaluation device can display the identified $CO_2$ content on a screen, convey it via a wireless or wire-conducted data interface to a display device or computing device, etc. At least one predetermined extreme value for the $CO_2$ content can also be stored in the evaluation device, the evaluation device outputting a warning signal, for example a warning light or a warning sound, when the value exceeds or falls below that extreme.

Advantageous embodiments and refinements are evident from the further descriptions herein and from the description with reference to the Figures.

According to a refinement, the pores have a pore diameter between 1 nm and 500 nm. The pore diameter measured by the Barrett-Joyner-Halenda (BJH) method, which underestimates pore diameter by about 1 to 1.5 nm, and before functionalization, may be between 1 nm and 20 nm, more particularly between 1.1 nm and 5 nm, in particular between 1.1 nm and 4 nm. The pores can furthermore have a pore diameter between 5 nm and 500 nm, more particularly between 8 nm and 50 nm.

According to a further refinement, the porous material is metal-oxidic or semimetal oxidic, which may be $SiO_2$, more particularly periodically mesoporous $SiO_2$. Additionally in this context, the materials may have a three-dimensional pore structure, for example MCM-48.

According to a further refinement, the first chemically functional group has a $pK_b$ value between 12 and 0, which may be between 9 and 1, more particularly between 7 and 2, in particular between 5 and 2.5. The $pK_b$ value is the negative decadic logarithm of the base dissociation constant Kb.

According to a further refinement, the first chemically functional group is immovably joined to the porous material via a substantially covalent bond, which may be by way of a bond via an —$O_xSiR_{3-x}$—$(CH_2)_n$ group, where x=1 to 3, n=1 to 20, and R is in particular methyl, ethyl, or propyl. In the structural formula above, "O" is to denote oxygen, "Si" silicon, "C" carbon, and "H" hydrogen. "Immovably joined" is to be understood to mean in particular that the chemically functional group is immobilized. This is, in particular, a substantially covalent bond. A joining unit of this kind is also called a "linker."

According to a further refinement, the at least one first chemically functional group is a primary, secondary, or tertiary amine group, for example aminopropyl, N-methylaminopropyl, N-phenylaminopropyl, N,N-dimethylaminopropyl, and/or N,N-diethylaminopropyl.

The at least one chemically functional group can also be a diamine group, for example N-(2-aminoethyl)-3-aminopropyl, furthermore a group having three or more amino functionalities, for example N—[N-(2-aminoethyl)-2-aminoethyl]-3-aminopropyl.

The at least one chemically functional group can also be an ethanolamine group, for example bis(2-hydroxyethyl)-3-aminopropyl.

The at least one chemically functional group can also be an aminidine group, for example N-(4,5-dihydroamidazolyl) propyl.

The at least one chemically functional group can moreover also be a guanidine group, a pyridine group, a triamine group, a polyamine group, and/or an imidazole group.

The pores of the porous material can also each have several of the aforesaid chemically functional groups, or also others that react in alkaline fashion with water. The aforementioned propyl groups can also represent examples of other hydrocarbon units of different lengths. The aforementioned propyl groups can simultaneously represent a connection to a silicon atom by which in turn a connection to an oxidic surface of the porous material can be implemented.

Groups which may also be used are those first chemically functional groups which are hydrophilic, i.e. which promote incorporation of water into the pores. Advantageous for this are aminopropyl, N-2-aminoethyl-3-aminopropyl, bis(2-hydroxyethyl)-3-aminopropyl, N—[N-(2-aminoethyl)-2-aminoethyl]-3-aminopropyl, or groups that carry a polyethylene imine unit.

According to a further refinement, a surface of the absorber device has at least one second chemically functional group. The second chemically functional group is a hydrophilic group, in particular N-propylgluconamide, hydroxymethyl, propyltrimethylammonium chloride, a group having or made up of at least one polyol unit, a group having or made up of at least one ethylene glycol unit, and/or a group having or made up of at least one silanol unit.

Alternatively, the second chemically functional group can be a hydrophobic group, in particular a hydrocarbon group or a fluorinated hydrocarbon group. The surface of the absorber device is in particular a surface that is in contact with the fluid or is capable of being brought into contact with the fluid.

A capillary condensation behavior, a polarity behavior, a conductivity behavior, and an effective internal pore diameter of the surface can be influenceable by a configuration of the at least one second chemically functional group on the surface of the absorber device.

The surface of the absorber device has at least one further chemically functional group. The at least one further chemically functional group is embodied to improve an ability of the absorber device to attach to metals, and may be an amine group, an ethylenediamine group, or a thiol group, in particular mercaptopropyl. Metallic electrodes of the electrode device can as a result be better able to attach to the absorber device. The surface of the absorber device is in particular a surface at which electrodes of the electrode device are mounted or to be mounted. This third groups can be identical to one of the aforementioned first or second groups.

According to a further refinement, the apparatus encompasses a temperature sensor device for identifying a fluid temperature value of a fluid temperature of the fluid. The temperature sensor device is joined to the evaluation device. The evaluation device is embodied to identify the $CO_2$ content of the fluid using the fluid temperature value, identified by way of the temperature sensor device, of the fluid temperature of the fluid. It is thereby possible to calculate more precisely back to the $CO_2$ partial pressure of the fluid.

According to a further refinement, the apparatus encompasses a heating device that is disposed on the absorber device. The absorber device is heatable by way of the heating device to an operating temperature of the absorber device having a predetermined operating temperature value, and holdable at the predetermined operating temperature value of the operating temperature. The evaluation device is embodied to identify the $CO_2$ content of the fluid using predetermined operating temperature value. It is thereby possible to calculate more precisely back to the $CO_2$ partial pressure of the fluid.

According to a refinement, the method according to the present invention furthermore has the steps of: baking out the absorber device in order to regenerate the absorber device, the absorber device being heated, for a time period between 1 s and 1000 s, to a baking-out temperature having a baking-out temperature value between 40° C. and 200° C., in particular for a time period between 2 s and 100 s to a baking-out temperature having a baking-out temperature value between 50° C. and 120° C.; and bringing the absorber device, in particular by heating and/or cooling, to an operating temperature having a predetermined operating temperature value, measurement taking place when the absorber device has assumed the operating temperature having the predetermined operating temperature value, and evaluation being accomplished using the predetermined operating temperature value. It is thereby possible to calculate more precisely back to the $CO_2$ partial pressure of the fluid.

According to a further refinement, the method according to the present invention furthermore has the step of: measurement of a fluid temperature value of a fluid temperature of the fluid, evaluation being accomplished using the measured fluid temperature value. It is thereby possible to calculate more precisely back to the $CO_2$ partial pressure of the fluid.

The present invention is explained in further detail below with reference to the exemplifying embodiments depicted in the schematic Figures of the drawings.

In all the Figures, identical or functionally identical elements and apparatuses are labeled, unless otherwise indicated, with the same reference characters.

DETAILED DESCRIPTION

Figure 1:
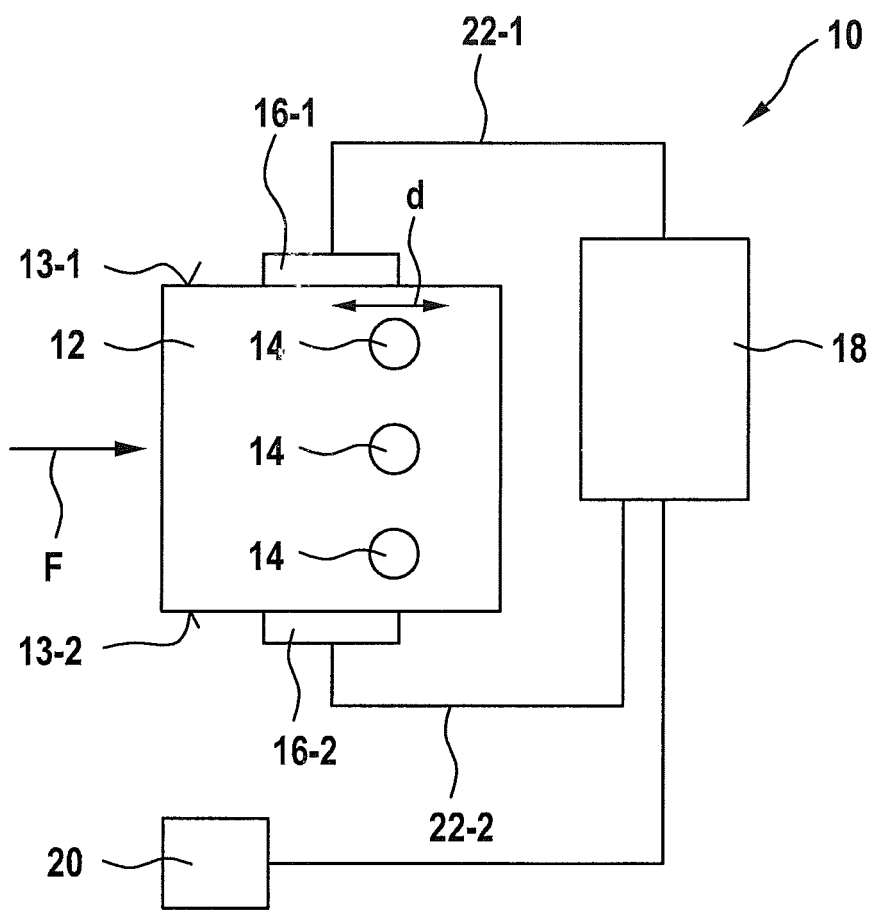
FIG. 1 is a schematic block diagram of an apparatus for identifying a $CO_2$ content of a fluid F, according to a first embodiment of the present invention.

FIG. 1 is a schematic block diagram of an apparatus 10 for identifying a $CO_2$ content of a fluid F, according to a first embodiment of the present invention. The size relationships in FIG. 1 are not to scale, but rather are highly distorted for better comprehension.

FIG. 1 shows an absorber device 12 of apparatus 10, which is made substantially of a porous material. Absorber device 12 is located above a surface of absorber device 12 in contact with fluid F. The surface encompasses, in particular, pores 14 of the porous material or is constituted, principally or entirely, by pores 14. Fluid F can flow past the surface of absorber device 12 or can rest on it. Pores 14 of the porous material of absorber device 12 each have a diameter d. Different pores can also have different values for their diameter d.

A first metallic electrode 16-1 of an electrode device 16-1, 16-2 for electrical contacting of absorber device 12 is disposed on a first lateral surface 13-1 of the absorber device. A second metallic electrode 16-2 of electrode device 16-1, 16-2 for electrical contacting of absorber device 12 is disposed on a second lateral surface 13-2 of the absorber device. First lateral surface 13-1 faces away from second lateral surface 13-2, and vice versa. The first and/or second metallic electrode 16-1, 16-2 can be made, for example, of platinum, gold, silver, or aluminum, or can encompass such a metal.

First and second electrodes 16-1, 16-2 are connected to an evaluation device 18 of apparatus 10 via a respective supply lead 22-1, 22-2. An electrical property of absorber device 12 is measurable by way of the evaluation device in order to identify the $CO_2$ content of the fluid.

A fluid temperature value of a fluid temperature of fluid F is identifiable by way of a temperature sensor device 20. Temperature sensor device 20 is joined to evaluation device 18. The evaluation device is embodied to identify the $CO_2$ content of the fluid using the fluid temperature value, identified by way of the temperature sensor device, of the fluid temperature of the fluid.

One of the methods according to the present invention described below can be executable by way of apparatus 10.

According to the first embodiment, pores 14 are relatively small mesopores having pore diameters (according to the Barrett-Joyner-Halenda (BJH) method and before functionalization) having values between 1.1 nm and 4 nm. For purposes of comprehensibility, in FIG. 1 the number of pores 14 is exaggeratedly small and the size of pores 14 is exaggeratedly large.

Pores 14 of the porous material have first chemically functional groups. The first chemically functional groups are joined to the porous material. The first chemically functional groups have the property of reacting in alkaline fashion with water, and in particular are amine groups, diamine groups, aminidine groups, or ethanolamine groups. Silanes can be used for corresponding functionalization, for example 3-aminopropyltrimethoxysilane, 2,2-dimethoxy-1,6-diaza-2-silacyclooctane, bis(2-hydroxyethyl)-3-aminopropyltriethoxysilane, N-(3-triethoxysilylpropyl)-4,4-dihydroimidazole, and/or 3-(trimethoxysilylpropyl)ethylenediamine.

Pores 14 optionally have further hydrophilic groups, for example N-propylgluconamide units, which are likewise covalently attached via silane units.

This embodiment is suitable in particular for a conductometric measurement principle, i.e. an identification of the $CO_2$ content of the fluid based on a conductivity, measured by way of evaluation device 18, of absorber device 12 that is in contact with the fluid. A voltage, in particular, can therefore be applied by way of evaluation device 18 to absorber device 12.

Figure 2:
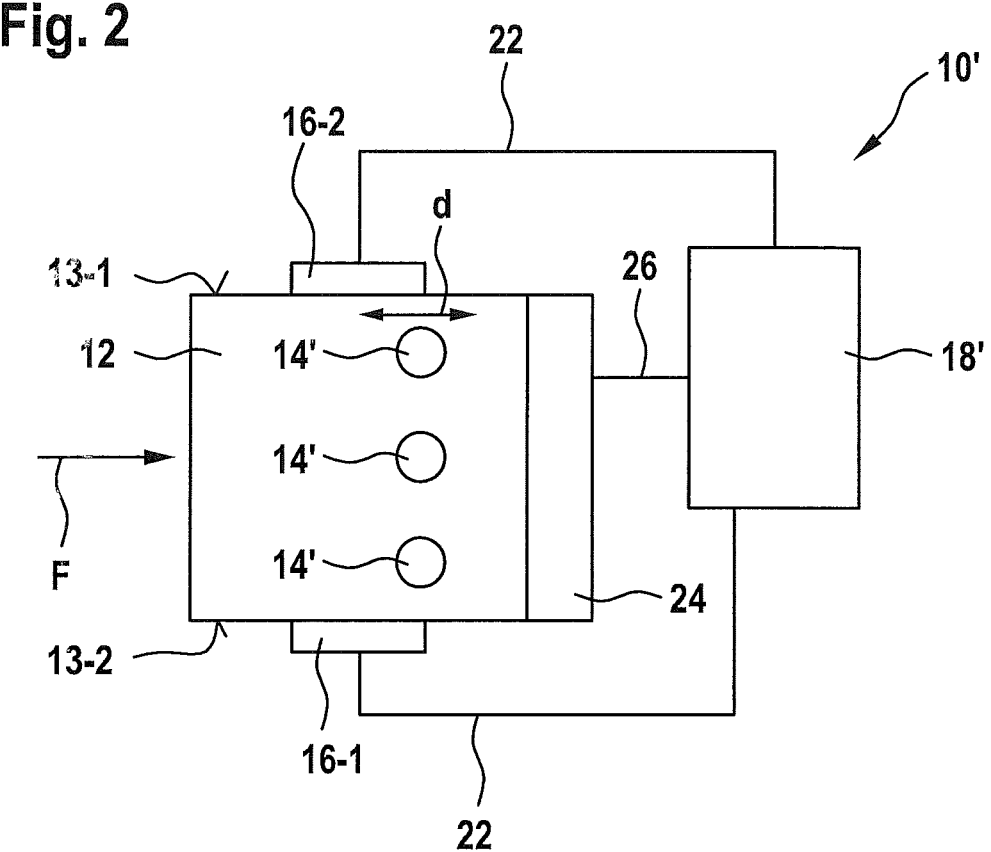
FIG. 2 is a schematic block diagram of an apparatus for identifying a $CO_2$ content of a fluid F, according to a second embodiment of the present invention.

FIG. 2 is a schematic block diagram of an apparatus 10' for identifying a $CO_2$ content of a fluid F, according to a second embodiment of the present invention. One of the methods according to the present invention described below can be executable by way of apparatus 10'.

The second embodiment is a variant of the first embodiment, apparatus 10' according to the second embodiment having, instead of temperature sensor apparatus 20 according to the first embodiment, a heating device 24 that is connected via power and data leads 26 to evaluation device 18' of apparatus 10'. Heating device 24 can in particular be a membrane-based microheater platform onto which the porous material of absorber device 12 is applied.

Heating device 24 is disposed on absorber device 12. Absorber device 12 is heatable by way of heating device 24 to an operating temperature of absorber device 12 having a predetermined operating temperature value, and is holdable at the predetermined operating temperature value of the operating temperature. Evaluation device 12 is embodied to determine the $CO_2$ content of the fluid using the predetermined operating temperature value.

The capillary condensation effect is not utilized according to the second embodiment. Pores 14' according to the second embodiment have pore diameters in the range from 5 nm to 500 nm, which may be from 8 nm to 50 nm. For purposes of comprehensibility, in FIG. 2 the number of pores 14' is exaggeratedly small and the size of pores 14' is exaggeratedly large.

Pores 14' have ethanolamine groups as a first chemically functional group. The surface of absorber device 12 is additionally equipped with hydrophobic groups. This can be achieved, for example, by treating the surface with butyldimethyl(dimethylamino)silane after partial functionalization with the ethanolamine groups. This produces, as a function of the partial pressure of $CO_2$ in fluid F, in particular in air as fluid F, a carbamate. What is produced in particular with a 2-hydroxyethyl-functionalized secondary amine, for example a 2-hydroxyethyl-3-aminopropyl group, is a cyclic carbamate.

Cyclic carbamates have a high dielectric constant. Apparatus 10' according to the third embodiment is thus advantageously capacitively measurable. In other words, evaluation device 18' is embodied to measure a capacitance of absorber device 12 as a function of the $CO_2$ content of fluid F.

Absorber device 12 having the properties of pores 14, and the substances, according to the first embodiment as described above can also be combined with heating device 24 according to the second embodiment. Absorber device 12 having the properties of pores 14, and the selected substances, according to the second embodiment as described above can likewise also be combined with temperature sensor device 20.

Figure 3:
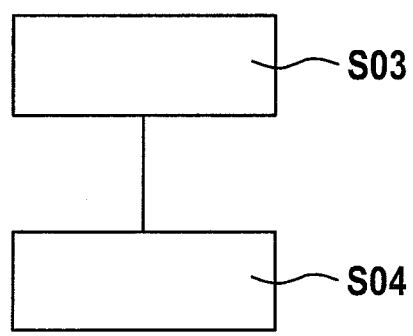
FIG. 3 is a schematic flow chart to explain a method for identifying a $CO_2$ content of a fluid, according to a third embodiment of the present invention.

FIG. 3 is a schematic flow chart to explain a method for identifying a $CO_2$ content of a fluid, according to a third embodiment of the present invention. The method can be carried out in particular using one of the apparatuses 10; 10' according to the first or the second embodiment.

In a step S03, an electrical property of absorber device 12 that is in contact with fluid F is measured via an electrode device 16-1, 16-2 mounted on absorber device 12. Absorber device 12 is made of a porous material. Pores 14; 14' of the porous material have at least one first chemically functional group, the first chemically functional group being joined, in particular immovably, to the porous material; and the first chemically functional group having the property of reacting in alkaline fashion with water. For this, a predefined electrical voltage and/or an electrical current can be applied by way of evaluation device 18; 18' to absorber device 12, for example as described below in detail below. Application of the voltage and/or current can be accomplished via electrode device 16-1, 16-2.

In a step S04, the measured electrical property of absorber device 12 is evaluated in order to identify the $CO_2$ content of fluid F.

Figure 4:
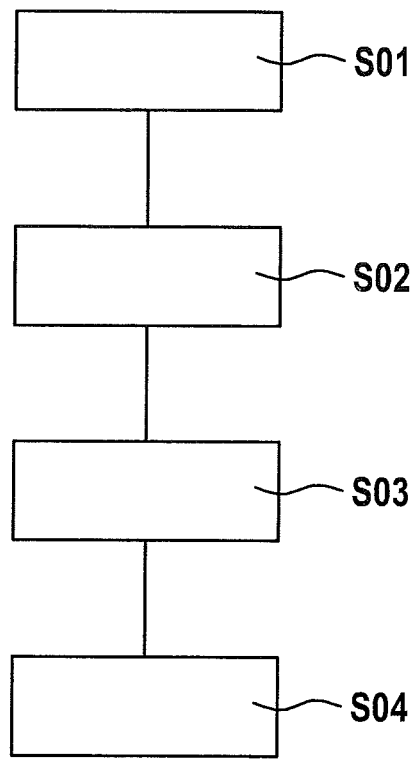
FIG. 4 is a schematic flow chart to explain a method for identifying a $CO_2$ content of a fluid, according to a fourth embodiment of the present invention.

FIG. 4 is a schematic flow chart to explain a method for identifying a $CO_2$ content of a fluid, according to a fourth embodiment of the present invention.

The method according to the fourth embodiment is a variant of the method according to the third embodiment, and as compared therewith additionally has the following steps:

In a step S01, absorber device 12 is baked out in order to regenerate absorber device 12. For this, absorber device 12 is heated for a time period between 1 s and 0 s to a baking-out temperature having a baking-out temperature value between 40° C. and 200° C., in particular for a time period between 2 s and 1000 s to a baking-out temperature having a baking-out temperature value between 50° C. and 120° C.

In a step S02, absorber device 12 is brought to an operating temperature having a predetermined operating temperature value. Measurement S03 takes place only once absorber device 12 has assumed the operating temperature having the predetermined operating temperature value. Evaluation S04 is accomplished using the predetermined operating temperature value.

Figure 5:
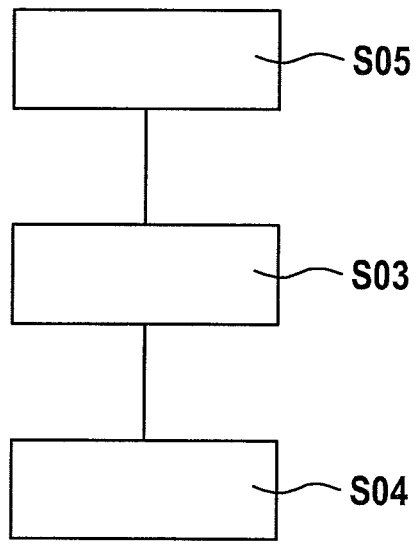
FIG. 5 is a schematic flow chart to explain a method for identifying a $CO_2$ content of a fluid, according to a fifth embodiment of the present invention.

FIG. 5 is a schematic flow chart to explain a method for identifying a $CO_2$ content of a fluid, according to a fifth embodiment of the present invention. The method according to the fourth embodiment is a variant of the method according to the third embodiment, and as compared therewith additionally has the following steps:

In a step S05 a fluid temperature value of a fluid temperature of fluid F is identified, for example by measurement e.g. using temperature sensor device 20. Evaluation S04 is accomplished using the measured fluid temperature value.

Although the present invention has been described above with reference to exemplary embodiments, it is not limited thereto but rather is modifiable in numerous ways. In particular, the invention can be changed or modified in a multiplicity of ways without deviating from the essence of the invention.

In the context of measurement and evaluation of a conductivity of absorber device 12, advantageously a constant direct current or a constant DC voltage is applied to absorber device 12, and the respective other variable (voltage or current) is detected by way of evaluation device 18; 18'. Evaluation device 18; 18' can be embodied correspondingly.

Voltage ramps having various rates can be traversed in order to obtain, from the current characteristic curves that are obtained, additional information about chemical and physical properties of the system, in particular of fluid F and of absorber device 12. The voltages or currents to be applied depend on the particular configuration of the apparatus according to the present invention.

In the context of measurement and evaluation of a change in the impedance of absorber device 12 by way of evaluation device 18; 18', advantageously an AC excitation voltage having a low amplitude is applied to absorber device 12, and a resulting current response is evaluated. Optionally, a DC component of the excitation voltage can be blended in.

A frequency dependence of polarization effects that are present can be utilized by measuring at different fixed frequencies or by using frequency ramps. For example, a change in the resonant frequency of an oscillator circuit can be measured. The porous material of absorber device 12 acts here substantially as a dielectric of a capacitor, the physical properties of which change as a function of the fluid F, for example a gas atmosphere, that is present. A variant of this kind is advantageous in particular for the use of a wireless apparatus to identify a $CO_2$ content: the change in resonant frequency can be read out directly, via a coupled antenna, using an active reading device.

Existing ASIC architectures of MEMS technology can be drawn upon in part for measuring the change both in conductivity and in capacitance.

What is claimed is:

1. An apparatus for identifying a $CO_2$ content of a fluid, comprising:
   an absorber device having a porous material, the absorber device being contactable with the fluid;
   pores of the porous material having at least one hydrophilic first chemically functional group joined to the porous material inside the pores of the porous material, and the first chemically functional group having a property of reacting with water to produce hydroxide ions, a surface of the absorber device having at least one third chemically functional group joined to the surface of the absorber device, and the at least one third chemically functional group being embodied to improve an ability of the surface of the absorber device to attach to metals;

an electrode device disposed on the surface of the absorber device and is electrically connected to the absorber device; and an evaluation device electrically connected to the electrode device, by which an electrical property of the absorber device is measurable to identify the $CO_2$ content of the fluid.

2. The apparatus of claim 1, wherein the pores have a pore diameter between 8 nm and 50 nm.

3. The apparatus of claim 1, wherein the porous material is metal-oxidic or semimetal-oxidic.

4. The apparatus of claim 1, wherein the first chemically functional group has a $pK_b$, value between 12 and 0.

5. The apparatus of claim 1, wherein the first chemically functional group is joined to the porous material immovably via a substantially covalent bond.

6. The apparatus of claim 1, wherein the first chemically functional group includes a primary, secondary, or tertiary amine group, diamine group, triamine group, polyamine group, ethanolamine group, aminidine group, guanidine group, pyridine group, and/or imidazole group.

7. The apparatus of claim 1, wherein a surface of the absorber device includes at least one hydrophilic second chemically functional group; the second hydrophilic chemically functional group being N-propylgluconamide, hydroxymethyl, propyltrimethylammonium chloride, a group having a polyol unit, having an ethylene glycol unit, or having a silanol unit.

8. The apparatus of claim 1, wherein a surface of the absorber device includes at least one second chemically functional group, the second chemically functional group being a hydrophobic group.

9. The apparatus of claim 1, further comprising:
a temperature sensor device to identify a fluid temperature value of a fluid temperature of the fluid, the temperature sensor device being joined to the evaluation device, the evaluation device being configured to identify the $CO_2$ content of the fluid using the fluid temperature value, which is identified using the temperature sensor device, of the fluid temperature of the fluid.

10. The apparatus of claim 1, further comprising:
a heating device disposed on the absorber device;
wherein the absorber device is heatable by the heating device to an operating temperature of the absorber device having a predetermined operating temperature value and being holdable at the predetermined operating temperature value of the operating temperature; and
wherein the evaluation device is configured to identify the $CO_2$ content of the fluid using the predetermined operating temperature value.

11. The apparatus of claim 1, wherein the third chemically functional group is selected from the group consisting of a primary, secondary, or tertiary amine group, diamine group, triamine group, polyamine group, ethanolamine group, aminidine group, guanidine group, pyridine group, imidazole group, ethylenediamine group, a thiol group, mercaptopropyl, N-propylgluconamide, hydroxymethyl, propyltrimethylammonium chloride, and/or a group having a polyol unit, having an ethylene glycol unit, or having a silanol unit.

12. The apparatus of claim 1, wherein the electrode device comprises a metallic electrode.

13. A method for identifying a $CO_2$ content of a fluid, the method comprising:
measuring an electrical property of an absorber device that is in contact with the fluid, via an electrode device mounted on a surface of the absorber device, the absorber device being made of a porous material, pores of the porous material having at least one hydrophilic first chemically functional group being joined to the porous material inside the pores of the porous material, and the first chemically functional group having a property of reacting with water to produce hydroxide ions, the surface of the absorber device having at least one third chemically functional group joined to the surface of the absorber device, and the at least one third chemically functional group being embodied to improve an ability of the surface of the absorber device to attach to metals; and
evaluating the measured electrical property of the absorber device to identify the $CO_2$ content of the fluid.

14. The method of claim 13, further comprising:
heating the absorber device for a time period between 1 s and 1000 s at temperature between 40° C. and 200° C.; and
bringing the absorber device to an operating temperature having a predetermined operating temperature value, measurement occurring when the absorber device has assumed the operating temperature having the predetermined operating temperature value;
wherein evaluation is performed using the predetermined operating temperature value.

15. The method of claim 13, further comprising:
measuring a fluid temperature value of a fluid temperature of the fluid;
wherein evaluation is performed using the measured fluid temperature value.

16. The method of claim 13, wherein the third chemically functional group is selected from the group consisting of a primary, secondary, or tertiary amine group, diamine group, triamine group, polyamine group, ethanolamine group, aminidine group, guanidine group, pyridine group, imidazole group, ethylenediamine group, a thiol group, mercaptopropyl, N-propylgluconamide, hydroxymethyl, propyltrimethylammonium chloride, and/or a group having a polyol unit, having an ethylene glycol unit, or having a silanol unit.

17. The method of claim 13, wherein the electrode device comprises a metallic electrode.

* * * * *